United States Patent [19]

Smith et al.

[11] Patent Number: 5,165,928
[45] Date of Patent: Nov. 24, 1992

[54] BIOLOGICAL CONTROL OF PHYTOPHTHORA BY GLIOCLADIUM

[75] Inventors: Victoria L. Smith, Branford, Conn.; Wayne F. Wilcox; Gary E. Harman, both of Geneva, N.Y.

[73] Assignee: Cornell Research Foundation, Inc., Ithaca, N.Y.

[21] Appl. No.: 630,244

[22] Filed: Dec. 19, 1990

Related U.S. Application Data

[63] Continuation-in-part of Ser. No. 271,143, Nov. 14, 1988, Pat. No. 4,996,157.

[51] Int. Cl.$^5$ .............................................. A61K 35/70
[52] U.S. Cl. ................................................. 424/93 Q
[58] Field of Search ..................................... 424/93 Q

[56] References Cited

U.S. PATENT DOCUMENTS

| 4,489,161 | 12/1984 | Papavizas | 435/254 |
| 4,996,157 | 2/1991 | Smith et al. | 424/93 Q |

OTHER PUBLICATIONS

Jeffers et al, 1982, Phytopathology, 72:533–528.
Wilcox, in 1987 New York State Pesticide Recommendations, Cornell University, Ithaca, N.Y. p. 533.
Abd-El Moity et al, 1982, Phytopathology, 72:396–400.
Abd-El Moity et al, 1981, Phytopath. Z., 100:29–35.
Ohr et al, 1973, Phytopathology, 63:965–973.
Chet et al, 1981, Phytopathology, 71:286–290.
Elad et al, 1982, Plant 7 Soil, 66:279–281.
Ruppel et al, 1983, Crop Protection, 2:399–408.
Jordan et al, 1978, Ann. Appl. Biol., 89:139–141.
Marois et al, 1982, Plant Dis., 66:1166–1168.
Chet et al, 1981, Microb. Ecol., 7:29–38.
Hadar et al, 1984, Phytopathology, 74:106–110.
Harman et al, 1983, Seed Sci. & Technol., 11:893–906.
Sivan et al, 1984, Phytopathology, 74:498–501.
Papavizas, 1985, Ann. Rev. Phytopathol., 23:23–54.
Hoitink et al, 1986, Ann. Rev. Phytopathol., 24:93–114.
Ellis et al, 1986, Plant Disease, 70:24–26.
Nelson et al, 1983, Phytopathology, 73:1457–1462.
Kraft et al, 1983, Plant Dis., 67:1234–1237.
Lumsden, R. D., et al, Phytopathology, vol. 79, No. 3, 361–366 (1989).
Wilton, J. H., et al, Phytopathology, vol. 72, No. 7, 1010–1011 (1982).
Phytopathology, vol. 80, No. 9, pp. 880–885 (1990).

Primary Examiner—Douglas W. Robinson
Assistant Examiner—Jean C. Witz

[57] ABSTRACT

Certain strains of Trichoderma and Gliocladium protect plants against diseases caused by Phytophthora spp. when applied to root system biosphere, e.g., *P. cactorum* caused root rot and crown and collar rot in apple tree seedlings and *P. sojae* caused stem and root rot in soybeam plants.

5 Claims, No Drawings

BIOLOGICAL CONTROL OF PHYTOPHTHORA BY GLIOCLADIUM

The work on apples herein was carried out with Government support under Grant No. USDA 87-CRSR-22992, awarded by the United States Department of Agriculture. The Government has certain rights in any invention relating to the work on apples.

CROSS REFERENCE TO RELATED APPLICATION

This application is a continuation-in-part of application Ser. No. 07/271,143 filed Nov. 14, 1988, now U.S. Pat. No. 4,996,157.

BACKGROUND OF THE INVENTION

Crown and collar rot, caused by at least four Phytophthora spp. (Jeffers et al, 1982, *Phytopathology*, 2:533:538) is a widespread and economically serious problem of apples throughout the Northeast US. In New York State, this disease appears to be the most common biological cause of premature tree decline and death, and in Pennsylvania, many growers have abandoned the horticulturally-desirable MM 106 rootstock because of high crown rot incidence or its perceived threat. Because no single approach to the control of Phytophthora crown rot has proved reliable, growers have been advised to adopt an integrated or additive disease management strategy, utilizing a combination of site selection, site modification, rootstock selection, and chemical treatments where appropriate (Wilcox, In: 1987 New York State Pesticide Recommendations. Cornell University, Ithaca, N.Y. 533 pp). However, the possibility of introducing a biological control agent as an additional component of such a program has heretofore been largely ignored.

Stem and root rot of soybeans caused by *Phytophthora sojae* Kaufmann and Gerdemann (also denoted *Phytophthora megasperma* forma specialis *glycinea*) is also a widespread and serious problem.

Species of Trichoderma and Gliocladium have been shown to provide varying levels of biological control of a number of important soil-borne plant pathogens, including *Sclerotium cepivorum* (Abd-el Moity et al, 1982, *Phytopathology*, 72:396–400; Abd-el Moity et al, 1981, *Phytopath. Z.*. 100:29–35), *Armillaria mellea* (Ohr et al, 1973, *Phytopathology*, 63:965-973), *Rhizoctonia solani* (Chet et al, 1981, Phytopathology, 71:286-290; Elad et al, 1983, *Plant and Soil*, 279-281; Ruppel et al, 1983, *Crop Protect.*, 2:399-408), *Verticillium dahliae* (Jordan et al, 1978, Ann. Appl. Biol., 89:139-141; Marios et al, 1982, *Plant Dis.*, 66:1166-1168) and Pythium spp. (Chet et al, 1981, *Microb. Ecol.*, 7:29-38; Hadar et al, 1984, *Phytopathology*, 74:106-110; Harman et al, 1983, *Seed Sci & Technol.*, 11:893-906; Sivan et al, 1984, *Phytopathology*, 74:498-501). While there have been many recent advances in the use of Trichoderma spp. as biological control agents (Papavizas, 1985, *Ann. Rev. Phytopathol.*, 23:23-54), to date there have been no concerted efforts made to use these fungi to control diseases caused by soil-borne Phytophthora spp., the economic importance of such diseases and the close relationship of the Phytophthora and Pythium genera notwithstanding.

Despite the lack of direct evidence, there exists correlative evidence that certain Trichoderma spp. may be involved in the biological control of several diseases caused by Phytophthora spp., e.g., *T. viride* versus heart rot of pineapple caused by *P. parasitica* (Papazivas, 1985, supra) More compelling correlative evidence is supplied by the well-documented ability of composted hardwood bark (CHB) to provide control of Phytophthora disease of woody plants when incorporated into their rhizospheres (Hoitink et al, 1986, *Ann. Rev. Phytopathol.*, 24:93-114), including control of crown rot of apple under field conditions (Ellis et al, 1986, *Plant Dis*, 70:24-26), and the related documentation that the addition of CHB to a container potting mix resulted in a 100 to 100,000 fold increase in the population levels of *T. harzianum* in this rooting medium (Nelson et al, 1983, Phytopathology, 3:1457-1462).

It has been recently pointed out that the potential of Trichoderma spp. for use as biological control agents has been studied primarily as an end in itself rather than as a synergistic or additive component in a broader integrated pest management system (Papavizas, 1985, supra). Nevertheless, there are several studies in which such an approach has been attempted successfully, e.g., methyl bromide plus Trichoderma for the control of *Armillaria mellea* (Ohr, 1973, supra), and *T. harzianum* plus fungicide for the control of root rot and damping off of pea caused by *Pythium ultimum* (Kraft et al. 1983, Plant Dis. 67:1234-1237).

DESCRIPTION OF THE INVENTION

This invention relates to novel strains of Trichoderma and Gliocladium spp. which are useful in controlling plant diseases caused by Phytophthora spp. such as root rot, crown rot, and collar rot, and methods for their use.

In preferred embodiments of methods of use, novel strains of Trichoderma and Gliocladium are used to control root, crown and collar rot in apple seedlings and trees that is incited by *Phytophthora cactorum* and to control stem and root rot of soybean plants that is incited by *Phytophthora sojae* Kaufmann and Gerdemann. The word "plants" is used herein to include seedlings as well as mature plants.

The Trichoderma and Gliocladium species of the invention ar isolated and obtained in biologically pure cultures and are applied to the biosphere of the root system of the plant to be protected in an amount sufficient to colonize and populate the plant root system biosphere, thereby controlling (i.e., reducing the incidence or severity of or eliminating) Phytophthora spp. caused plant diseases. The phrases "biosphere of the root system" and "plant root biosphere" are used herein to mean the soil where seeds are planted, where seedlings are transplanted or where mature plants are growing.

A method herein of controlling plant diseases incited by *Phytophthora sojae* Kaufmann and Gerdemann, especially stem and root rot in soybean plants, comprises applying to the plant root biosphere of the plants to be protected a biosphere colonizing amount of a biocontrol agent selected from the group consisting of:
Gliocladium virens, 031 (ATCC 20903);
*Gliocladium virens*, 035 (ATCC 20904); and
*Gliocladium virens*, 041 (ATCC 20906).
Each of the Gliocladium spp. indicated herein by an ATCC No. are deposited at the American Type Culture Collection, 12301 Parklawn Drive, Rockville, Md. 20852, under that number, to meet the requirements of the Budapest Treaty on the International Recognition of the Deposit of Microorganisms for the Purposes of Patent Procedure.

The Trichoderma and Gliocladium biocontrol agents herein are readily applied in the form of an inoculum and preferred inocula are described below and a sufficient inoculum typically should provide a biosphere colonizing amount of between $10^4$ to $10^6$ colony-forming-units of Trichoderma and Gliocladium per gram of soil to assure establishment of the beneficial Trichoderma and Gliocladium in the plant root biosphere. Depending on the climate conditions, soil conditions, the amount of Phytophthora spp. present in the biosphere, and the possible presence of other competing microorganisms in the biosphere being inoculated, lesser or greater amounts of Trichoderma or Gliocladium can also be used to establish the Trichoderma or Gliocladium of the invention in the plant biosphere.

Preferably, the Trichoderma or Gliocladium is added to the plant biosphere in the form of a preformed inoculum comprising a carrier which the Trichoderma or Gliocladium have colonized and if desired, water and/or nutrients or trace minerals which assist the growth of the Trichoderma or Gliocladium. Carriers such as peat and/or wheat bran, vermiculite, pasteurized soil and the like can be employed. The inoculum is readily prepared by mixing the carrier and Trichoderma or Gliocladium, usually with water, and any other desired adjuvants, in amounts to cause colonization of the Trichoderma or Gliocladium on the carrier. The mixture is then incubated until the Trichoderma or Gliocladium is soundly established on the carrier so as it, in turn, provides a suitable vehicle for the Trichoderma or Gliocladium to colonize the soil biosphere to which the inoculum is subsequently added.

The Trichoderma or Gliocladium containing inoculum or other compositions containing the Trichoderma or Gliocladium can be applied by means known in the art, depending on its physical state.

The following Example I demonstrates the effectiveness of biocontrol agents herein in controlling Phytophthora cactorum caused disease in apple tree seedlings.

EXAMPLE I

Materials and Methods

Sample collection

Soil was collected from orchards in Orleans County, N.Y. on Jun. 5, 1987. Samples were collected from around the crowns of apple and cherry trees growing on heavy, wet, and/or frequently-flooded soil; trees were asymptomatic for Phytophthora root and crown rot. Samples were decimally diluted in sterile distilled water and plated on a medium selective for Trichoderma spp. (TSM, i.e., Trichoderma Selective Medium, Smith et al, 1990, *Phytopathology,* 80, 880–885). Isolates of candidate biocontrol fungi were collected from the plates by mass transfer of conidia after 5 days inculation on the lab bench. Isolates were identified to species using Rifai's key (Rifai, 11969, *Mycol. Pap.,* 116:1–56).

Soil also was collected from fields in Livingston County, N.Y., on November 1987. Samples were taken from fields from which Aphanomyces root rot of pea had disappeared. Individual soil cores were taken along an arbitrary transect through the field; cores from a particular field were bulked and thoroughly mixed. Samples were decimally diluted in sterile distilled water and plated on TSM. Isolates were collected and identified as outlined above.

Soil also was collected from a wet grassy area on Cornell University's Vegetable Research Farm located in Geneva, Ontario County, N.Y. Soil samples were diluted as outlined above and plated on TSM. Plates were incubated at 11° C.

In vitro interactions with Phytophthora spp

Candidate isolates were paired with P. cactorum and P. cambivora on corn meal agar and incubated at 10°, 16° and 22° C. Cultures were observed daily and any overgrowth of Phytophthora by Trichoderma or Gliocladium was noted. Any antibiotic activity of Trichoderma or Gliocladium against Phytophthora was noted. Antibiotic activity was defined as any inhibition of radial growth of Phytophthora by Trichoderma or Gliocladium.

Greenhouse screen

Candidate isolates that were able to grow well at low temperature (10°–11°) and exhibited antibiotic activity against Phytophthora were chosen for further evaluation in the greenhouse.

Preparation of soil soil was prepared by mixing 4 l pasteurized soil, 8 l vermiculite, and 2 l water. All ingredients were placed in a large plastic bag and thoroughly mixed.

Preparation of Trichoderma and Gliocladium inocula a mixture of peat and wheat bran (1:1 v/v; moistened with 1 part distilled water) was autoclaved twice, on two successive days, 15 min each at 15 lbs pressure. After thorough cooling, the peat-bran preparation was inoculated with 4–6 disks, each 5 mm diameter, cut from the actively-growing margin of a colony of the candidate isolate growing on corn meal agar (Difco). Peat-bran inoculum was incubated on the lab bench for 7 to 10 days. Inoculum of candidate isolates was thoroughly mixed with soil both alone and in combination with soil infested with P. cactorum, at a rate of approximately 20 ml/3.25 l soil, resulting in $10^4$ to $10^6$ colony-forming-units of the candidate isolate per gram of soil mix.

Preparation of Phytophthora inoculum a mixture of V8 juice broth and vermiculite (3:5 v/v; V8 broth of 200 ml V8 juice, 800 ml distilled water, and 2 grams $CaCO_3$/l) was autoclaved twice, on two successive days, 15 min. each at 15 lbs pressure. After thorough cooling, the V8-vermiculite preparation was inoculated with 4–6 disks, each 5 mm diameter, cut from the actively-growing margin of a colony of *P. cactorum* on corn meal agar. V8-vermiculite was incubated on the lab bench for 2 to 3 wk. V8-vermiculite then was placed on 4 layers of cheesecloth and washed free of V8 juice. The final preparation consisted primarily of oospores and sporangia in a vermiculite carrier. Inoculum was thoroughly mixed into soil at a rate of 250 ml/12 l soil.

After addition of all inocula, soil was allowed to stand at room temperature for at least 12 hr, but not more than 24 hr, prior to use.

Five sprouted seeds from open-pollinated McIntosh apples were planted per pot, and each Trichoderma or Gliocladium ×Phytophthora combination was replicated five times. Immediately prior to potting, a sample (approximately 15 grams fresh weight) was taken from each soil lot and ten-gram subsamples were decimally diluted and plated on TSM. Initial levels of Trichoderma and Gliocladium were estimated after five days incubation at room temperature.

Pots containing seedlings were placed in a greenhouse maintained at 18° C. After 2 weeks pots containing seedlings were flooded to a depth of 1 cm for 72 hr, to induce zoospore production and subsequent infection by Phytophthora. During flooding, leaf disk baits were used to estimate relative levels of Phytophthora in each pot (Wilcox et al, 1985, *Phytopathology*, 75:648-653). Seven to 10 days after conclusion of flooding, plants in each pot were evaluated for the number of hypocotyl lesions, percent root rot, and total plant weight.

Data Analysis

Presence of Phytophthora and Trichoderma or Gliocladium were treated as qualitative variables in analysis of variance, with plant weight as the independent variable. Correlation coefficients between all variables (number of leaf disk baits colonized, number of hypocotyl lesions, percent root rot, total plant weight, and initial CFU Trichoderma or Gliocladium) were calculated.

RESULTS

Approximately 67 strains initially were screened in vitro. Of these, 27 showed sufficient antibiotic activity to be tested in the greenhouse. Of those tested in the greenhouse, 3 gave moderate protection against Phytophthora and 7 were very effective in reducing damage by *P. cactorum* (Table 1). Data on these strains is given in Table 2. For plants grown in the presence of Trichoderma or Gliocladium alone, there was a significant increase in the total plant weight, compared to plants grown in potting medium without Trichoderma. For plants in the Trichoderma or Gliocladium ×Phytophthora combinations, total plant weight was increased and percent root rot was less than for plants in the presence of Phytophthora alone (Table 2).

TABLE 1

Selection of isolates effective against Phytophthora spp.

| Source of isolates | Total number of isolates | Effective in vitro | Effective in planta |
| --- | --- | --- | --- |
| Cornell Vegetable Farms | 23 | 10 | 4 |
| Orleans Co., New York | 30 | 6 | 2 |
| Livingston Co., New York | 14 | 11 | 4 |

TABLE 2

Efficacy of strains of Biocontrol Agent against Phytophthora spp.

| treatment | total plant weight (gm) | percent change[a] | root rot rating |
| --- | --- | --- | --- |
| Isolates from orchard soils | | | |
| P. cambivora | 3.54 | — | 2.2 |
| P. cactorum | 3.48 | — | 2.8 |
| T. harzianum Rifai #30 (ATCC 20902)[b] X P. cactorum | 3.74 | 7.5 | 2.0 |
| Isolates from the Vegetable Research Farm | | | |
| P. cambivora | 1.47 | — | 3.4 |
| P. cactorum | 1.86 | — | 3.4 |
| Trichoderma viride Pers. ex S.F. Gray #14X (ATCC 20898) P. cambivora | 3.27 | 122.45 | 1.8 |
| Trichoderma koningii Oud. #23X (ATCC 20899) P. cambivora | 1.69 | 14.97 | 3.8 |
| T. viride #24X (ATCC 20900) P. cambivora | 3.49 | 137.41 | 1.6 |
| T. koningii #25X (ATCC 20901) P. cambivora | 2.07 | 40.82 | 2.8 |
| Trichoderma viride Pers. ex S.F. Gray #14X (ATCC 20898) P. cactorum | 2.23 | 19.89 | 2.8 |
| Isolates from the Vegetable Research Farm | | | |
| Trichoderma koningii Oud. #23X (ATCC 20899)[b] P. cactorum | 3.40 | 82.80 | 2.6 |
| T. viride #24X (ATCC 20900) P. cactorum | 2.03 | 9.14 | 3.8 |
| T. koningii #25X (ATCC 20901) P. cactorum | 3.71 | 99.46 | 2.0 |
| Isolates from Aphanomyces-suppressive soils | | | |
| P. cactorum | 3.31 | — | 1.9 |
| Gliocladium virens Miller, Giddens & Foster #31X (ATCC 20903) P. cactorum | 4.47 | 35.0 | 1.3 |
| G. virens #35X (ATCC 20904) P. cactorum | 3.77 | 13.9 | 2.0 |
| T. viride #36X (ATCC 20905) P. cactorum | 4.05 | 22.36 | 1.7 |
| G. virens #41X (ATCC 20906) P. cactorum | 3.50 | 5.74 | 1.5 |
| T. harzianum #43X (ATCC 20907) P. cactorum | 3.38 | 2.11 | 1.7 |

[a]percent change over Phytophthora alone treatments.
[b]each of the Trichoderma spp. indicated by ATCC No. in this table are deposited at the American Type Culture Collection, Rockville, MD under that number to meet the requirements of the Budapest Treaty on the International Recognition of the Deposit of Microorganisms for the Purposes of Patent Procedure.

[a]percent change over Phytophthora alone treatments.
[b]each of the species indicated by ATCC No. in this table are deposited at the American Type Culture Collection, Rockville, MD under that number to meet the requirements of the Budapest Treaty on the International Recognition of the Deposit of Microorganisms for the Purposes of Patent Procedure.

DISCUSSION

The ten isolates noted in Table 2 have activity against *Phytophthora cactorum*, both in vitro and in planta. These are the first Trichoderma and Gliocladium found with activity against this genus of pathogenic fungi. The isolates also were tested for tolerance to the fungicide metalaxyl in vitro. Radial growth on corn meal agar amended with fungicide was not affected at concentrations as high as 10 ug/ml. The results of this study indicate that these isolates of Trichoderma and Gliocladium are useful in an integrated program to manage *P. cactorum* on susceptible trees.

The following Example II demonstrates the effectiveness of biocontrol agents herein in controlling *Phytophthora sojae* Kaufmann and Gerdemann caused stem and root rot in soybean plants.

EXAMPLE II

The six biocontrol isolates that gave the best level of control of *Phytophthora cactorum* on apple seedlings in Example I above and in other studies were further examined for their ability to control stem and root rot of soybeans caused by *Phytophthora sojae* Kaufmann and Gerdemann. The six biocontrol isolates used were *Gliocladium virens*, 031 (ATCC 20903); *Trichoderma harzianum*, 034; *Gliocladium virens*, 035 (ATCC 20904); *Trichoderma viride*, 036 (ATCC 20905); *Trichoderma hamatum*, 037; and *Gliocladium virens*, 041 (ATCC 20906); and these are respectively referred to as 031, 034, 035, 036, 037, and 041 below.

Biocontrol inoculum was prepared as in Example I with incubation being carried out for 1 week.

Inoculum of *Phytophthora sojae* was produced by the method of preparation for Phytophthora inoculum in Example I with incubation being carried out for 3 weeks.

Prepared inocula were added to a steam-pasteurized potting medium (2 volumes fine vermiculite: 1 volume sandy loam), at a rate of 0.6% (v:v) for the biocontrol isolates (approximately $10^5$ c.f.u./g. soil mix) and 1.0% (v:v) for *Pythophthora sojae* (10 cm$^3$/1000 cm$^3$ soil mix). Soybeans of the cultivar "Sloan" (highly susceptible to *Phytophthora sojae* caused stem and root rot) or "Williams" (moderately susceptible) were then grown in 0.95 L plastic pots filled with potting medium plus inoculum by either (a) planting five ungerminated seeds approximately 2.5 cm deep (referred to as DIRECT SEEDED in the Tables below); or (b) transplanting three seedlings (first trioliate leaf exposed) from unamended potting medium into inoculated medium (referred to as TRANSPLANTED in the table below). For both planting methods, there were five replicate pots for each cultivar x biocontrol isolate x pathogen (+/−) treatment.

One week after planting, all pots were flooded for a 48-hr period by plugging the drainage hole and adding water until 5-10 mm of free water collected on the soil surface. Flooding treatments were repeated twice more at weekly intervals, then 5 wk after initiation of the experiment all plants were removed from the pots, the roots were washed free of soil, and plant growth was assessed on the basis of total root and shoot fresh weights of all plants in an individual pot; in pots receiving inoculum of *P. sojae*, the frequency of stem lesion occurrence and/or seedling damping off also was determined as a measure of disease incidence. The experiment was repeated thrice in a greenhouse maintained at a temperature of 18°-25° C.

The data are presented in terms of mean values for five replicate pots per experiment. Means within a column not followed by a common letter are significantly different (P=0.05, Waller-Duncan).

Tables 3, 4, and 5 below respectively present the data for the three repeats of the experiment.

The term "Fresh Weight" in Tables 3, 4, and 5 means weight of plant parts as they were harvested, i.e., without drying.

TABLE 3

| | | Sloan | | | Williams | | |
|---|---|---|---|---|---|---|---|
| | | Fresh Weight (g) | | % plants w/stem | Fresh Weight (g) | | % plants w/stem |
| Isolate # | Phytophthora | roots | shoots | lesion | roots | shoots | lesion |
| DIRECT SEEDED | | | | | | | |
| 035 | No | 17.8 a | 23.3 a | 0.0 b | 14.5 ab | 22.7 a | 0.0 a |
| 036 | No | 17.2 ab | 22.6 a | 0.0 b | 15.3 a | 19.9 abc | 0.0 a |
| None | No | 16.1 ab | 19.4 b | 0.0 b | 13.9 abc | 17.1 cd | 0.0 a |
| 031 | No | 16.1 ab | 22.6 a | 0.0 b | 12.1 bcd | 21.1 a | 0.0 a |
| 041 | No | 15.8 abc | 19.9 b | 0.0 b | 15.5 a | 22.4 a | 0.0 a |
| 034 | No | 15.7 bc | 19.9 b | 0.0 b | 15.1 a | 21.9 a | 0.0 a |
| 037 | No | 13.8 c | 20.0 b | 0.0 b | 12.2 bcd | 20.1 ab | 0.0 a |
| 035 | Yes | 7.8 d | 13.5 c | 0.0 b | 11.9 cd | 18.2 bc | 0.0 a |
| 041 | Yes | 6.2 de | 10.9 d | 4.0 b | 8.2 ef | 12.1 e | 0.0 a |
| 031 | Yes | 6.0 de | 10.6 d | 0.0 b | 10.5 de | 15.3 de | 6.6 a |
| 034 | Yes | 4.7 e | 8.0 e | 0.0 b | 8.7 ef | 12.3 e | 0.0 a |
| 037 | Yes | 4.1 ef | 6.0 ef | 6.6 b | 5.0 g | 8.5 f | 13.4 b |
| 036 | Yes | 2.4 fg | 4.3 fg | 10.0 b | 6.3 fg | 8.5 f | 6.6 a |
| None | Yes | 1.4 g | 3.0 g | 35.0 a | 4.5 g | 6.7 f | 14.0 b |
| TRANSPLANTED | | | | | | | |
| 035 | No | 15.0 a | 14.1 a | 0.0 c | 15.8 ab | 15.7 a | 0.0 c |
| 034 | No | 14.5 a | 13.6 a | 0.0 c | 15.7 abc | 15.3 a | 0.0 c |
| 031 | No | 11.5 b | 11.3 b | 0.0 c | 15.8 ab | 14.7 a | 0.0 c |
| None | No | 11.5 b | 9.6 bc | 0.0 c | 13.8 bc | 12.5 bc | 0.0 c |
| 037 | No | 10.1 b | 9.6 bc | 0.0 c | 14.4 abc | 14.3 ab | 0.0 c |
| 036 | No | 9.9 bc | 9.1 cd | 0.0 c | 16.3 a | 14.3 ab | 0.0 c |
| 041 | No | 9.4 bc | 9.5 cd | 0.0 c | 13.4 c | 13.7 ab | 0.0 c |
| 035 | Yes | 7.8 cd | 7.9 cd | 13.2 abc | 9.2 de | 8.6 d | 13.4 bc |
| 031 | Yes | 5.8 de | 7.8 d | 6.6 bc | 9.9 d | 10.7 c | 0.0 c |
| 041 | Yes | 4.8 ef | 4.6 e | 26.6 abc | 8.0 de | 7.4 d | 0.0 c |
| None | Yes | 3.9 efg | 4.3 e | 26.4 abc | 7.3 e | 6.7 d | 13.2 bc |
| 034 | Yes | 2.7 fg | 4.3 e | 33.0 ab | 7.3 e | 8.3 d | 0.0 c |
| 036 | Yes | 2.6 g | 2.9 e | 20.0 abc | 7.1 e | 6.9 d | 33.2 a |
| 037 | Yes | 2.5 g | 3.1 e | 40.0 a | 8.4 de | 8.3 d | 19.8 ab |

TABLE 4

| Isolate # | Phytoph-thora | Sloan Fresh Weight (g) roots | Sloan Fresh Weight (g) shoots | Sloan % plants w/stem lesion | Williams Fresh Weight (g) roots | Williams Fresh Weight (g) shoots | Williams % plants w/stem lesion |
|---|---|---|---|---|---|---|---|
| DIRECT SEEDED | | | | | | | |
| 041 | No | 17.3 a | 18.8 ab | 0.0 c | 15.6 a | 19.8 ab | 0.0 b |
| 037 | No | 15.2 ab | 17.3 abc | 0.0 c | 16.2 a | 19.8 ab | 0.0 b |
| 036 | No | 14.7 bc | 19.7 a | 0.0 c | 17.7 a | 21.2 a | 0.0 b |
| 034 | No | 13.6 bc | 18.0 abc | 0.0 c | 11.8 bc | 18.7 bc | 0.0 b |
| 035 | No | 13.0 bc | 16.7 bc | 0.0 c | 11.6 bc | 16.4 cd | 0.0 b |
| 031 | No | 12.8 bc | 17.2 abc | 0.0 c | 12.8 b | 19.4 ab | 0.0 b |
| None | No | 12.7 c | 15.8 c | 0.0 c | 10.6 cd | 16.2 d | 0.0 b |
| 035 | Yes | 8.2 d | 11.5 d | 0.0 c | 9.0 de | 13.2 e | 0.0 b |
| 031 | Yes | 6.5 d | 8.9 e | 5.0 c | 9.0 de | 13.0 e | 4.0 b |
| 041 | Yes | 6.1 d | 8.1 e | 10.6 c | 9.4 d | 11.5 e | 0.0 b |
| 037 | Yes | 3.1 e | 4.3 f | 30.0 b | 7.0 ef | 9.1 fg | 10.0 b |
| 034 | Yes | 2.2 e | 3.4 f | 37.0 b | 5.6 fg | 7.9 gh | 17.4 b |
| 036 | Yes | 2.2 e | 3.7 f | 40.0 b | 8.9 d | 11.2 ef | 0.0 b |
| None | Yes | 1.7 e | 2.3 f | 71.0 a | 3.9 g | 6.2 h | 42.0 a |
| TRANSPLANTED | | | | | | | |
| 031 | No | 18.7 a | 16.0 ab | 0.0 e | 16.6 a | 18.8 b | 0.0 c |
| None | No | 16.4 b | 15.3 ab | 0.0 e | 16.8 a | 14.9 cde | 0.0 c |
| 036 | No | 16.0 bc | 16.4 ab | 0.0 e | 15.6 ab | 16.7 c | 0.0 c |
| 034 | No | 15.7 bc | 17.0 a | 0.0 e | 16.9 a | 21.8 a | 0.0 c |
| 037 | No | 15.2 bc | 15.4 ab | 0.0 e | 14.0 bc | 16.4 c | 0.0 c |
| 041 | No | 14.6 bc | 14.9 b | 0.0 e | 14.2 bc | 16.2 cd | 0.0 c |
| 035 | No | 13.9 c | 12.6 c | 0.0 e | 13.8 c | 14.1 e | 0.0 c |
| 035 | Yes | 9.2 d | 11.0 cd | 26.6 cd | 12.0 d | 14.5 de | 0.0 c |
| 041 | Yes | 8.3 d | 9.9 d | 6.6 de | 10.7 d | 11.5 f | 0.0 c |
| 031 | Yes | 7.6 de | 10.2 d | 0.0 e | 11.2 d | 12.0 f | 0.0 c |
| None | Yes | 5.5 ef | 7.1 e | 66.6 ab | 8.0 e | 8.0 g | 13.2 bc |
| 036 | Yes | 4.6 f | 6.8 e | 46.6 bc | 7.5 e | 8.5 g | 26.4 ab |
| 034 | Yes | 4.3 fg | 6.5 e | 53.4 ab | 7.5 e | 8.5 g | 19.8 ab |
| 037 | Yes | 2.2 g | 3.6 f | 73.4 a | 7.0 e | 7.3 g | 33.4 a |

TABLE 5

| Isolate # | Phytoph-thora | Sloan Fresh Weight (g) roots | Sloan Fresh Weight (g) shoots | Sloan % plants survival | Williams Fresh Weight (g) roots | Williams Fresh Weight (g) shoots | Williams % plants w/stem lesion |
|---|---|---|---|---|---|---|---|
| DIRECT SEEDED | | | | | | | |
| 036 | No | 26.7 a | 21.0 a | 96.0 a | 22.1 a | 25.5 a | 100.0 a |
| 037 | No | 21.6 b | 19.4 ab | 92.0 a | 16.7 bcd | 18.2 d | 84.0 b |
| 035 | Yes | 19.2 bc | 17.1 bc | 100.0 a | 20.3 a | 19.5 cd | 96.0 ab |
| 041 | No | 18.9 bc | 19.5 ab | 100.0 a | 16.9 bc | 22.3 b | 96.0 ab |
| 034 | No | 17.0 cd | 19.8 ab | 92.0 a | 15.1 b-e | 21.6 bc | 92.0 ab |
| 031 | Yes | 16.6 cd | 13.9 de | 68.0 b | 16.7 bcd | 15.0 e | 88.8 ab |
| 031 | No | 15.6 cd | 18.7 ab | 96.0 a | 14.1 de | 18.2 d | 92.0 ab |
| 035 | No | 15.1 d | 17.1 bcd | 96.0 a | 16.5 bcd | 22.8 ab | 100.0 a |
| None | No | 13.7 de | 14.8 cde | 96.0 a | 12.8 e | 13.9 ef | 92.0 ab |
| 041 | Yes | 13.7 de | 20.2 ab | 92.0 a | 14.4 cde | 21.0 bc | 88.8 ab |
| 036 | Yes | 11.4 e | 12.7 ef | 76.0 b | 15.1 b-e | 15.2 e | 92.0 ab |
| 034 | Yes | 10.3 ef | 9.4 g | 64.0 b | 15.1 b-e | 21.6 bc | 92.0 ab |
| 037 | Yes | 6.8 f | 9.9 fg | 72.0 b | 9.6 f | 11.9 f | 68.0 c |
| None | Yes | 1.5 g | 1.0 h | 8.0 c | 9.6 f | 8.0 g | 48.0 d |

| Isolate # | Phytoph-thora | Sloan Fresh Weight (g) roots | Sloan Fresh Weight (g) shoots | Sloan % plants w/stem lesion | Williams Fresh Weight (g) roots | Williams Fresh Weight (g) shoots | Williams % plants stem lesion |
|---|---|---|---|---|---|---|---|
| TRANSPLANTED | | | | | | | |
| 034 | No | 26.5 a | 18.6 a | 0.0 d | 19.3 cde | 18.7 abc | 0.0 c |
| 036 | No | 25.4 a | 17.8 a | 0.0 d | 23.7 a | 20.4 ab | 0.0 c |
| 041 | No | 24.5 ab | 16.8 abc | 0.0 d | 19.6 b-e | 18.6 bc | 0.0 c |
| 037 | No | 22.0 bc | 18.0 a | 0.0 d | 22.9 abc | 20.1 ab | 0.0 c |
| 035 | No | 21.8 bc | 14.9 cd | 0.0 d | 18.9 de | 15.8 cde | 0.0 c |
| None | No | 20.3 cd | 15.3 bcd | 0.0 d | 21.7 a-d | 18.1 b-d | 0.0 c |
| 031 | No | 18.9 de | 13.7 de | 0.0 d | 23.2 ab | 18.2 bcd | 0.0 c |
| 035 | Yes | 18.0 de | 15.6 bcd | 6.6 cd | 16.4 ef | 15.3 de | 0.0 c |
| 041 | Yes | 16.8 e | 17.3 ab | 13.4 cd | 24.1 a | 21.5 a | 13.2 bc |
| 031 | Yes | 9.8 f | 8.3 f | 26.6 bc | 16.4 ef | 15.3 de | 0.0 c |
| 036 | Yes | 8.3 fg | 12.3 e | 26.6 bc | 12.9 f | 13.0 e | 46.6 a |
| 034 | Yes | 7.5 fg | 7.0 f | 40.0 b | 12.8 f | 13.2 e | 0.0 c |
| 037 | Yes | 6.8 g | 7.5 f | 93.4 a | 16.0 ef | 15.8 cde | 33.2 ab |
| None | Yes | 6.8 g | 6.7 f | 46.6 b | 13.4 f | 13.2 e | 13.2 bc |

The data of Tables 3, 4 and 5 indicate *Gliocladium virens* 031, 035 and 041 provide significant levels of biological control of *Phytophthora sojae* in soybeans as evidenced by lower disease incidences (i.e. fewer plants with stem lesions or greater seedling survival) and by increased root and shoot weights relative to plants that received no biocontrol isolate and that the Gliocladium isolates were statistically significantly more effective than the Trichoderma isolates in most cases.

Many variations of inventive embodiments will be obvious to those skilled in the art. Thus, the inventive embodiments are defined by the claims.

What is claimed is:

1. A method of controlling plant diseases incited by *Phytophthora sojae* Kaufmann and Gerdemann which comprises applying to the plant root biosphere of the plants to be protected a biosphere colonizing amount of a biocontrol agent selected from the group consisting of:

*Gliocladium virens*, 031 (ATCC 20903);
*Gliocladium virens*, 035 (ATCC 20904); and
*Gliocladium virens*, 041 (ATCC 20906).

2. The method of claim 1 wherein the plant disease incited by *Phytophthora sojae* Kaufmann and Gerdemann is stem and root rot in soybean plants.

3. The method of claim 2 wherein the biocontrol agent is Gliocladium virens, 031 (ATCC 20903).

4. The method of claim 2 wherein the biocontrol agent is *Gliocladium virens*, 035 (ATCC 20904).

5. The method of claim 2 wherein the biocontrol agent is *Gliocladium virens*, 041 (ATCC 20906).

* * * * *